(12) United States Patent
Wigfall

(10) Patent No.: US 9,131,704 B2
(45) Date of Patent: Sep. 15, 2015

(54) CARBON DIOXIDE BASED METHOD AND SYSTEM FOR THE HUMANE MASS CULLING OF POULTRY AND STERILIZATION OF REARING SHEDS

(71) Applicant: Tim Wigfall, Ashbourne (GB)

(72) Inventor: Tim Wigfall, Ashbourne (GB)

(73) Assignee: Linde Aktiengesellschaft, Munich (DE)

( * ) Notice: Subject to any disclaimer, the term of this patent is extended or adjusted under 35 U.S.C. 154(b) by 0 days.

(21) Appl. No.: 14/407,222

(22) PCT Filed: Jun. 11, 2013

(86) PCT No.: PCT/EP2013/001712
§ 371 (c)(1),
(2) Date: Dec. 11, 2014

(87) PCT Pub. No.: WO2013/185910
PCT Pub. Date: Dec. 19, 2013

(65) Prior Publication Data
US 2015/0157031 A1    Jun. 11, 2015

(30) Foreign Application Priority Data

Jun. 14, 2012  (EP) .................................... 12004490

(51) Int. Cl.
*A22B 3/00*    (2006.01)
*A22B 3/08*    (2006.01)
*B05B 15/02*   (2006.01)
*G01N 33/00*   (2006.01)

(52) U.S. Cl.
CPC ................. *A22B 3/005* (2013.01); *A22B 3/086* (2013.01); *B05B 15/025* (2013.01); *G01N 33/0036* (2013.01)

(58) Field of Classification Search
USPC ........................................ 452/57–61, 66, 173
See application file for complete search history.

(56) References Cited

U.S. PATENT DOCUMENTS

| 4,325,221 | A | * | 4/1982 | Grewar ............................. 62/63 |
| 5,141,156 | A | * | 8/1992 | Hoy et al. ..................... 239/135 |
| 5,394,643 | A | * | 3/1995 | Schmittmann .................. 43/124 |
| 5,487,699 | A | * | 1/1996 | Tyrrell et al. .................... 452/66 |
| 6,230,501 | B1 | * | 5/2001 | Bailey, Sr. et al. ............. 62/51.1 |
| 6,623,347 | B1 | * | 9/2003 | Grimsland et al. ............. 452/57 |

(Continued)

FOREIGN PATENT DOCUMENTS

| EP | 1 817 961 B1 | 4/2006 |
| WO | WO 2007/129100 A1 | 11/2007 |
| WO | WO 2008/128027 A1 | 10/2008 |

OTHER PUBLICATIONS

PCT International Search Report, Date of Mailing: Sep. 12, 2013, Authorized Officer: Elisabeth Vonk, 5 pages.

(Continued)

*Primary Examiner* — Richard Price, Jr.
(74) *Attorney, Agent, or Firm* — Joshua L. Cohen

(57) ABSTRACT

A method for humanely killing animals (2), particularly birds, includes spraying liquid $CO_2$ into a holding site (10) housing said animals so that said $CO_2$ is evaporated and said animals (2) are exposed to an atmosphere (3) in their holding site (10) containing gaseous $CO_2$, asphyxiating the animals (2) by exposing them to said atmosphere (3), and discharging a mixture of a purge gas (P) and at least one sterilizing agent (A) into the holding site. A related system (1) for humanely killing animals (2), particularly birds, is also provided.

14 Claims, 1 Drawing Sheet

(56) References Cited

U.S. PATENT DOCUMENTS

Figure 1:
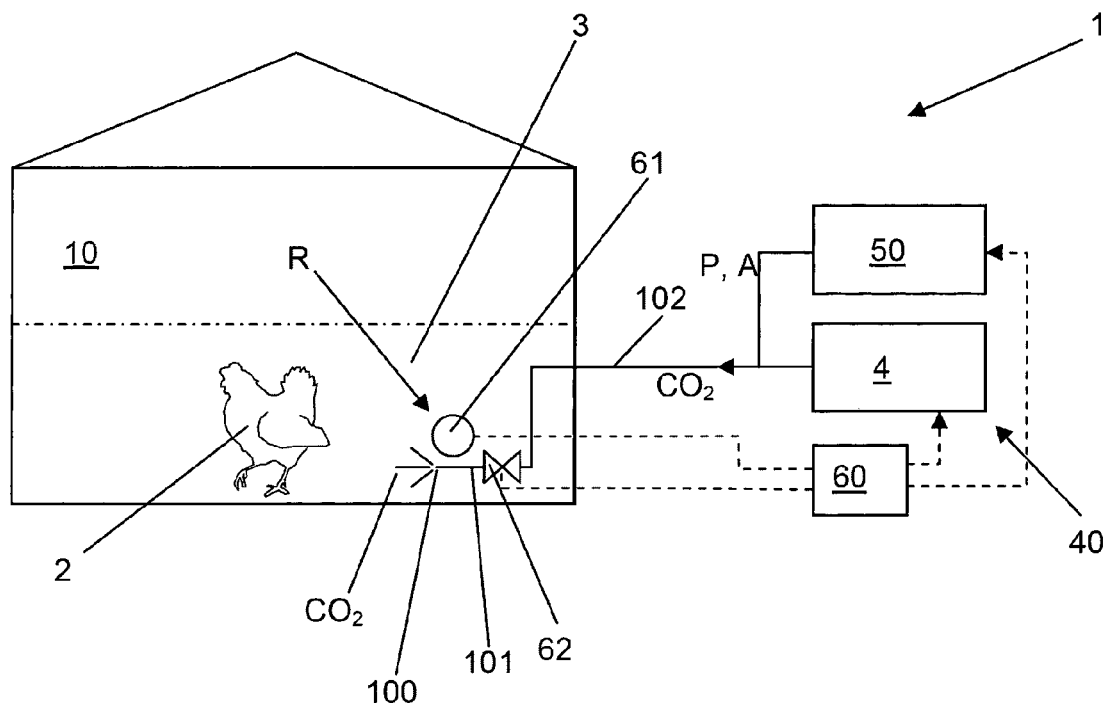

| | | | |
|---|---|---|---|
| 7,435,166 B2 * | 10/2008 | Benson et al. | 452/173 |
| 7,448,943 B1 * | 11/2008 | Woodford et al. | 452/66 |
| 7,771,255 B2 * | 8/2010 | Cattaruzzi | 452/57 |
| 8,029,342 B2 * | 10/2011 | Anderson et al. | 452/66 |
| 8,101,220 B2 * | 1/2012 | Garwood | 426/238 |
| 8,323,080 B2 * | 12/2012 | Lang et al. | 452/66 |
| 8,591,297 B2 * | 11/2013 | Lang et al. | 452/66 |
| 2007/0184081 A1 | 8/2007 | Benson et al. | |
| 2008/0254727 A1 | 10/2008 | Lang et al. | |

OTHER PUBLICATIONS

PCT Written Opinion, Date of Mailing: Sep. 12, 2013, Authorized Officer: Angel Rojo Galindo, 4 pages.

\* cited by examiner

CARBON DIOXIDE BASED METHOD AND SYSTEM FOR THE HUMANE MASS CULLING OF POULTRY AND STERILIZATION OF REARING SHEDS

The invention relates to a method and a system (device) for humanely killing animals, particularly birds.

To prevent further spreading of animal diseases, such as the bird flu, it may be necessary to kill the infected animals. This may be achieved by means of asphyxiation due to inhalation of gaseous $CO_2$ as described in EP 1 817 961 B1 for instance.

According thereto, the at least one animal (bird) to be culled is exposed to a carbon dioxide atmosphere at its holding site by spraying liquid carbon dioxide into the holding site, e.g. a pen (rearing shed).

Based on the above, the problem underlying the present invention is to further improve such a method by reducing the risk for an operator to become infected as well as by reducing the risk of spreading of viruses or other pathogenic agents whilst carrying out the culling and clean-up procedure.

According to the invention, this problem is solved by a method having the features of the claims.

According thereto—after having asphyxiated said animals by exposing them to said carbon dioxide ($CO_2$) atmosphere—a purge gas containing at least one sterilising agent is discharged into said holding side for sterilising the holding site or at least parts thereof before human entry and clean-up operations begin. In such a holding site, the animals, particularly in case of poultry such as chickens, may be free to roam but may also be held in smaller boxes provided in the holding site.

Thus, due to the invention, the holding site, e.g. a pen or other kinds of rearing sheds, can be quickly returned to normal atmospheric oxygen concentrations. Further, due to the sterilizing agent, the risk for operators and the risk of further spreading of diseases is significantly reduced.

Particularly, the sterilising agent is designed to eliminate (remove) or kill all forms of microbial life, including transmissible agents (such as fungi, bacteria, viruses, spore forms, etc.) being present on a surface or in an atmosphere in a rearing shed. In a variant of the invention, said purge gas comprises at least nitrogen and oxygen. According to an aspect of the invention, the purge gas may be air, which may be particularly taken from the non-contaminated atmosphere outside the holding site (rearing shed).

According to an embodiment, the sterilising agent may comprise ozone, wherein particularly the concentration of ozone is below 5 ppm, preferably below 1 ppm, preferably in a region between 0.3 and 0.05 ppm, particularly 0.1 ppm.

According to yet another embodiment of the invention, the sterilizing agent is a liquid upon mixing it with the purge gas (or comprises a liquid component) that is atomized into the purge gas before or upon discharging the purge gas into the holding site, i.e., the purge gas actually serves as a carrier of the sterilising agent.

In case of birds, the atmosphere, to which said birds are exposed to, preferably contains at least 45 vol % $CO_2$, which particularly allows for rendering the birds unconscious within 30 seconds. Preferably, this atmosphere is maintained until all the birds are dead, which will occur within approximately two minutes.

During spraying carbon dioxide into the holding site, an actual value of the oxygen and/or carbon dioxide concentration of said atmosphere to which the animals are exposed to is repeatedly or continuously sensed (or estimated) and the amount of carbon dioxide that is sprayed into the holding site per time is controlled such that said actual value approaches a pre-defined desired value, which may be—in case of the $CO_2$ concentration—the afore-mentioned 45 vol % $CO_2$.

In order to achieve a horizontally uniform distribution of $CO_2$ or lack of oxygen in a layer near the ground of the holding site where the $CO_2$ tends to accumulate and in which the birds to be culled reside, actual values of the oxygen and/or carbon dioxide concentration of said atmosphere are measured either repeatedly or continuously in different regions (locations) of the holding side (i.e. said layer) and the amounts of $CO_2$ that are sprayed into these regions per time are separately controlled such that the individual actual values approach a pre-defined desired value. Generally, in case of measuring oxygen concentration the actual values may also go below said desired value. In case of measuring $CO_2$ concentration the desired value may also be exceeded by the actual values.

Likewise, upon discharging said purge gas into said holding site, an actual value of either the oxygen concentration, the carbon dioxide concentration, or the concentration of said sterilizing agent of said atmosphere (or a combination of these quantities), to which the animals are exposed to, is preferably measured and discharging of said purge gas is controlled such that said actual value approaches a pre-defined desired value.

Also here, in order to allow for uniform purging, actual values of the oxygen concentration, the dioxide concentration, and/or the concentration of said sterilizing agent of said atmosphere, to which the animals are exposed to, may be measured in different regions of the holding site, and discharging of said purge gas may be controlled separately in each of these regions such that said actual values approach a pre-defined desired value. This allows one to return the atmosphere in the holding site, to which the animals have been exposed to, to normal atmospheric oxygen concentrations in a comparably uniform manner that allows humans to safely enter the holding site for conducting the clean-up operations after the culling.

Furthermore, the problem according to the invention is solved by a system (or system) for humanely killing animals, particularly birds (poultry), wherein the system according to the invention is particularly provided for being used in a method according to the invention.

The system according to the invention comprises a mobile liquid carbon dioxide vessel, which may be arranged on a suitable vehicle and forms part of a spraying means, which is designed to spray liquid carbon dioxide through a plurality of nozzles into a holding site of said animals so that said carbon dioxide is evaporated for generating an atmosphere in said holding site containing a lethal concentration of gaseous carbon dioxide, wherein the system comprises a purging means being designed to discharge a purge gas containing (carrying) at least one sterilising agent into said holding side for sterilising the holding site or at least parts thereof before human entry and clean-up operations begin.

According to an aspect of the invention, the purging means comprises an eductor being designed to atomize the sterilizing agent into the purge gas upon discharging the purge gas (and thus the sterilizing agent) into the holding site.

According to an aspect of the invention, such an eductor comprises a carrier gas nozzle protruding into a chamber of the eductor, wherein a carrier gas, here the purge gas, is introduced into said chamber via the carrier gas nozzle, while said liquid agent is introduced into said chamber via a separate inlet (e.g. below the carrier gas nozzle), wherein particularly the carrier gas nozzle faces a converging inlet nozzle connected to said chamber, which in turn is connected to a diverging outlet diffuser.

In this way said eductor is designed to utilize the energy in the form of pressure, which is in said carrier gas (e.g. the purge gas), to create a low pressure area in said chamber and, thereby, suck the liquid sterilising agent through said inlet into the chamber and mix it into the purge gas stream.

Further mixing, entrainment and atomisation of the liquid is then achieved as the gas velocity is accelerated by means of said venturi arrangement (i.e. the converging inlet nozzle followed by the diverging outlet diffuser). The fine "mist" of atomised liquid particles is then carried and dispersed into the general atmosphere when the purge gas stream is released from the outlet diffuser.

At ambient pressures (initially) present in the holding site, $CO_2$ is either gaseous or a liquid. In case liquid $CO_2$ is sprayed through nozzles and relaxed at a pressure below the triple point pressure, a mixture of carbon dioxide snow and gaseous $CO_2$ is formed which may block the nozzles (outlets).

Therefore, a feed pipe which may deliver the liquid $CO_2$ to a spray tube comprising said nozzles (outlets) is preferably pressurized by means of gaseous $CO_2$ before feeding liquid $CO_2$ into the feed pipe so that the pressure inside the feed tube is above the ambient pressure (in the holding side). Particularly, in case the pressure in the feed tube exceeds the triple point pressure, liquid $CO_2$ is fed into the feed tube, thus preventing the formation of carbon dioxide snow. Particularly, switching from gaseous to liquid $CO_2$ preferably takes place at a pressure of at least 5.2 bar, more preferably at a pressure of at least 5.5 bar, more preferably at a pressure of at least 6.0 bar.

Pressure buildup may be achieved in the feed tube by dimensioning the nozzles (outlets) such that the total cross-sectional area of the spray tube is smaller than the cross-sectional area of the feed tube. Thus, when feeding gaseous $CO_2$ into the feed tube, the necessary pressure buildup can be achieved.

Preferably, the nozzles (outlets) comprise diameters of less than 3 mm, preferably less than 2 mm, more preferably between 1 and 1.5 mm.

In order to control the generation of the $CO_2$-rich atmosphere leading to asphyxiation of the animals residing in the holding site as well as the purging procedure, the system comprises a controlling unit according to a further aspect of the invention, which is designed to control the amount of $CO_2$ and/or purge gas that is discharged into the holding site per time (e.g. by opening/closing valves).

For this, the system preferably comprises at least one sensor interacting with the controlling unit, which sensor is preferably designed to be arranged in said holding site, so as to preferably measure an actual value of the oxygen concentration due to discharging of carbon dioxide into the holding site (in addition also the carbon dioxide concentration may be measured), wherein the controlling unit is preferably designed to control the amount of carbon dioxide that is sprayed into the holding site per time (e.g. by opening/closing at least one valve) such that said at least one actual value being measured either repeatedly or continuously approaches a pre-defined desired value. Preferably, a plurality of sensors interacting with the controlling unit is employed, each sensor being configured to preferably measure an actual value of an oxygen concentration in an associated region of the holding site, in which the respective sensor is located, wherein the controlling unit is designed to separately control the amount of carbon dioxide sprayed into the respective region through at least one nozzle (outlet) being associated to the respective region (e.g. by opening/closing a respective valve) such that said actual values approach a pre-defined desired value (in a uniform manner).

Furthermore, with respect to purging, the system preferably comprises at least one sensor (which may be the at least one sensor described above) interacting with the controlling means, which sensor is designed to be arranged in said holding site, that is designed to measure either an actual value of an oxygen concentration (in addition also the carbon dioxide concentration and/or the concentration of the sterilizing agent may be measured), wherein the controlling unit is designed to control purging of said purge gas by means of said purging means (e.g. by opening/closing at least one valve) such that said actual value approaches a pre-defined desired value, wherein particularly the system comprises a plurality of sensors interacting with the controlling unit, each being configured to measure an actual value of an oxygen concentration in an associated region of the holding site, wherein the controlling unit is designed to control purging of said purge gas into the respective region of the holding site by means of the purging means (e.g. by opening/closing a respective valve) such that said actual values approach a pre-defined desired value, particularly so as to return the atmosphere in the holding site to which the animals have been exposed to, to normal atmospheric oxygen concentrations that allow humans to safely enter the holding site (for conducting the clean-up operations).

Particularly, before entry—as part of a controlled re-entry procedure—the $CO_2$ concentration is measured to ensure compliance with relevant occupational hygiene and health and safety standards for the work place.

In a variant of the method according to the invention the sterilization agent is introduced via purging with air, followed by a "dwell period" of no gas flow—to allow settlement and sterilization to take place (this will be immediate upon contact). Following the sterilization period a final stage purge with air (from the external atmosphere) is preferably conducted.

Dual action activated carbon & particulate filter type PPE respirators may be appropriate in any event for the protection of operators from potential respiratory problems (viral or chemical).

Further, when introducing a sterilizing agent into the rearing sheds, like ozone for instance, the concentration of such an agent may be measured, in order to be able to monitor concentrations of such agent that may pose a health risk to the operators conducting the cleaning procedure after the culling. Alternatively, the liquid volume of said agent applied to the eductors may be controlled in order to be able to estimate the concentration of such an agent in the rearing shed/holding site.

Summarizing, the system (and method) according to the invention can be rapidly deployed and redeployed and allows for easy assembly/installation and disassembly/removal as well as cleaning of "contact" items. Further, mass culling of especially birds can be performed humanely and controlled with as little stress as possible caused to the birds during the process. Finally, human contact with the birds is reduced during the culling procedure, thus avoiding risks to operators and also risk of spread of the disease.

Figure 2:
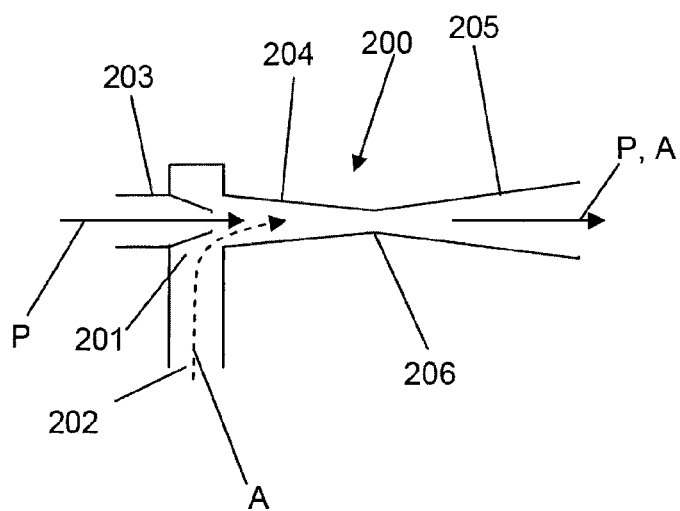

Further features and advantages of the present invention shall be described by means of a detailed description of an embodiment with reference to the Figures, wherein FIG. 1 shows a schematical illustration of a system/method according to the invention; and FIG. 2 shows an eductor used for mixing a sterilising agent into the purge gas for forming an aerosol.

FIG. 1 shows a system 1 that is particularly designed for the humane mass culling of poultry and commercially farmed avian species 2 in their rearing environment (holding site) 10.

The system (device) 1 is designed to kill the "targeted" birds 2 by means of asphyxiation. Because of its relatively high density (and therefore relative willingness to stay where it is required) $CO_2$ is used to displace the air/oxygen within the rearing building (holding site) 10.

For this, the system 1 comprises a mobile liquid $CO_2$ vessel 4 for storing the liquid $CO_2$ at a pressure between 10 bar and 20 bar. The vessel 4 is a part of a spraying means 40 that is designed to spray the liquid $CO_2$ into the holding site 10, wherein the liquid $CO_2$ is distributed via pipe work of the spraying means 40, which may consist of a feed tube 102 and a spray tube 101 connected thereto, to pre-determined regions (locations) R in the rearing shed 10 (only one such region is shown for example) via nozzles 100. During operation the liquid $CO_2$ is introduced into the shed 10 as a fine spray that is generated by means of said nozzles 100 provided on the spray tube 101 or some other pipe work. Preferably, before discharging of $CO_2$ starts, the feed tube 102 is pressurized by gaseous $CO_2$ from the vessel 4. Once the pressure in the feed tube 102 is above a pre-determined pressure (e.g. triple point pressure), liquid $CO_2$ from the vessel 4 is injected into the feed tube 102 and discharging of $CO_2$ via nozzles 100 into the holding site 10 starts.

Modern commercial bird rearing sheds 10 are often very large and therefore in order to rapidly achieve a lethal atmosphere 3 within the building 10 (i.e. to minimise stress to the birds 2) the spraying means 40 (gas injection system) is controlled by a controlling unit 60, for instance in the form of a programmable logic controller (PLC), that may be designed to control valves 62 associated to individual nozzles 100 or a group of nozzles, so that the amount of liquid $CO_2$ that is sprayed into a certain region R associated to such a nozzle 100 or group of nozzles 100 can be controlled for the individual region R so that an actual value of the oxygen concentration in the respective region R approaches a certain desired value, which may be the same for all regions R, thus allowing to achieve an at least horizontally uniform lack of oxygen for asphyxiation throughout the holding site 10. The respective oxygen concentration in a region R may be measured at successive points in time by means of a sensor 61 associated to the respective region R. Of course, also a simpler setup is conceivable, in which there is only one such sensor 61 for the whole holding site 10.

Having successfully carried out the cull, the next issue is how personnel can safely and rapidly gain entry to the rearing sheds 10 to remove the birds 2 and minimise the opportunity for contact with and spread of any disease causing agents during the cleaning-up process (the atmosphere 3 that is lethal to birds is also lethal to humans, harmful bacteria and viruses are also likely to be present in the atmosphere and on surfaces in the shed). The system 1 according to the invention therefore also integrates an "air purge" function with the introduction and distribution of a sterilising agent A so that the sheds 10 are returned to normal atmospheric oxygen concentrations and the internal environment of the shed 10 is sterilised before human entry and clean-up operations begin.

For this, when the $CO_2$-rich atmosphere has been maintained for a while such that the birds 2 are dead, discharging of $CO_2$ is stopped, and a purge gas P is fed through the afore-mentioned tubes 102, 101 by means of a purging means 50 (e.g. comprising a pump) into the holding site 10, i.e., to the regions R of the latter. Of course, the purge gas P may also be fed into the holding site 10 by said means 50 via a separate conduit.

The sterilizing agent A that is added to the purge gas P (e.g. air) or that forms a component of the purge gas P may be ozone (a powerful gaseous oxidising agent commonly used for sterilisation purposes) or proprietary liquid chemical sterilising formulations.

In the latter case, the liquid (sterilizing agent A) will be preferably atomised into the purge gas stream P via a gas eductor system. For this, the nozzles 100 can be formed as eductors 200 as shown in FIG. 2. Alternatively, the separate conduit for the purge gas P as mentioned above may comprise such eductors 200 for discharging the purge gas P and the sterilizing agent A into the holding site 10 in the form of an aerosol. The separate conduit may comprise valves that can be controlled by the controlling unit 60 in order to control the amount of purge gas P that is fed through said eductors 200 into the holding site 10. Said aerosol will then be distributed within the shed 10 by means of the carrier gas (purge gas) P to maximise its effectiveness, coverage and contact.

In detail, such an eductor 200 comprises a carrier gas nozzle 203 protruding into a chamber 201 of the eductor 200, wherein a carrier gas, here the purge gas P, is introduced into said chamber 201 via the carrier gas nozzle 203, while said liquid sterilising agent A is introduced into said chamber 201 via a separate inlet 202 that is designed to be connected to a container for storing the sterilising agent A, wherein particularly the carrier gas nozzle 203 aligns with a converging inlet nozzle 204 protruding from the chamber 201, which converging inlet nozzle 204 is in turn connected via a narrow region (diffuser throat) 206 to a diverging outlet diffuser 205, via which the aerosol formed out of the purge gas P and the agent A is discharged into the holding site 10. When the purge gas P enters the chamber 201 through said carrier gas nozzle 203 a low pressure region is created in the chamber such that said agent A is sucked into the chamber 201 and thereafter mixed into the purge gas stream P. Further mixing, entrainment and atomisation of the liquid agent A is then achieved as the purge gas is accelerated by means of inlet nozzle 204 and diffuser 205.

Again, also upon purging, the system 1 is preferably controlled and monitored by the controlling unit 60. For this, the sensors 61 measure the oxygen concentration, and purging of the purge gas P into the respective regions R (for instance through nozzles 100 or eductors 200) is controlled such that a non-harmful $CO_2$ (i.e. a sufficient oxygen) concentration is reached. Here, also the $CO_2$ concentration and/or the concentration of the sterilizing agent A may be measured (at least once before re-entry) and may also be controlled by the controlling unit 60 to get to concentrations that are not harmful for the personnel conducting the clean-up process.

Furthermore, the system may comprise a visual monitoring system that is designed to display information during the culling operation like the actual values of the oxygen concentration, and eventually also the $CO_2$-concentration, and/or the concentration of the sterilising agent in the holding site 10 or in the respective regions R of the holding site 10.

The system (device) 1 according to the invention may further comprise a simulation means (e.g. a computer and a software executed on the computer) that is designed to simulate (model) the culling procedure to enable the quick and easy design and customisation of the culling system 1. This enables the system 1 according to the invention to be successfully adapted to meet the wide variety of building challenges that it may be presented with in the field.

What is claimed is:
1. A method for humanely killing animals, particularly birds; comprising:
spraying liquid $CO_2$ into a holding site (10) housing said animals (2) and evaporating said $CO_2$;

exposing said animals to an atmosphere (3) in the holding site containing gaseous $CO_2$;

asphyxiating said animals by exposing to said atmosphere; and discharging a mixture of a purge gas (P) and at least one sterilizing agent (A) into the holding site.

2. The method of claim 1, wherein the discharging comprises returning the holding site to normal atmospheric oxygen concentration.

3. The method of claim 1, further comprising selecting the purge gas (P) from the group consisting of oxygen and nitrogen, air, and air from an atmosphere external to the holding site.

4. The method of claim 1, wherein the at least one sterilizing agent (A) comprises ozone.

5. The method of claim 1, wherein the at least one sterilizing agent (A) comprises a liquid mixed into the purge gas (P) for generating an aerosol to be discharged into the holding site.

6. The method of claim 1, further comprising:

measuring a value of oxygen concentration of said atmosphere to which the animals are exposed;

controlling the spraying of said 007 into the holding site such that said value approaches a pre-defined value;

measuring actual values of the oxygen concentration of said atmosphere to which the animals are exposed in different regions (R) of the holding site upon said spraying of said $CO_2$ into said different regions (R) such that said actual values of the oxygen approach the pre-defined value.

7. The method of claim 1, wherein the discharging further comprises:

measuring an actual value of an oxygen concentration, and at least one of an actual value of a $CO_2$ concentration and an actual value of a concentration of said at least one sterilizing agent (A) in said atmosphere;

controlling the discharging of the purge gas (P) into the holding site such that the actual values of the oxygen and at least one of the actual values of the $CO_2$ and sterilizing agent (A) concentrations of said atmosphere can be measured;

measuring actual values of the purge gas (P) concentration and at least the actual value of at least one of the $CO_2$ concentration and the at least one sterilizing agent (A) concentration in different regions (R) of said holding site; and controlling the discharging of the purge gas (P) into said regions (R) such that said actual values approach a pre-defined value for returning the atmosphere to normal atmospheric oxygen conditions for humans to enter the holding site.

8. A system for humanely killing animals, particularly birds, in a holding site, comprising:

spraying means (40) comprising a vessel (4) for storing liquid $CO_2$, and at least one nozzle in fluid communication with the spraying means to spray the liquid $CO_2$ into the holding site such that said liquid $CO_2$ is evaporated for generating an atmosphere (3) in said holding site containing gaseous $CO_2$; and purging means (50) for discharging a mixture of a purge gas (P) and at least one sterilizing agent (A) into said holding site.

9. The system of claim 8, wherein the purging means comprises an eductor (200) for receiving the at least one sterilizing agent (A) and the purge gas (P); and an outlet for discharging an aerosol of the mixture from the at least one sterilizing agent (A) and the purge gas (P) into the holding site.

10. The system of claim 8, further comprising a controlling unit (60) for controlling at least one of the spraying means and the purging means.

11. The system of claim 10, further comprising:

at least one sensor (61) coacting with the controlling unit to measure an actual value of an oxygen concentration in the no/ding site, the controlling unit controlling the spraying means responsive to said at least one sensor.

12. The system of claim 10, further comprising:

at least one sensor (61) coacting with the controlling unit to measure at least one of an actual value of an oxygen concentration, a $CO_2$ concentration, and a concentration of said sterilizing agent (A) in said holding site, the controlling unit controlling purging of said purge gas (P) by said purging means.

13. The system of claim 10, further comprising a plurality of sensors (61) coacting with the controlling unit to measure the actual value of an oxygen concentration in associated regions (R) of the holding site, the controlling unit controlling spraying of said liquid $CO_2$ into the associated regions (R) such that said actual values approach a pre-defined value.

14. The system of claim 10, further comprising a plurality of sensors (61) coacting with the controlling unit to measure at least one of the actual value of the oxygen concentration, a $CO_2$ concentration, and a concentration of said sterilizing agent (A) in associated regions (R) of the holding site, the controlling unit controlling the purging of said purge gas (P) by the purging means into the associated regions (R) such that said actual values approach a pre-defined value.

* * * * *

UNITED STATES PATENT AND TRADEMARK OFFICE
CERTIFICATE OF CORRECTION

PATENT NO. : 9,131,704 B2  
APPLICATION NO. : 14/407222  
DATED : September 15, 2015  
INVENTOR(S) : Tim Wigfall Page 1 of 1

It is certified that error appears in the above-identified patent and that said Letters Patent is hereby corrected as shown below:

In the Claims

Column 7, Claim 6, line 23, delete "007" and insert therefore -- $CO_2$ --.

Column 8, Claim 11, line 25, delete "no/ding" and insert therefore -- holding --.

Signed and Sealed this  
Nineteenth Day of January, 2016

Michelle K. Lee  
*Director of the United States Patent and Trademark Office*